(12) United States Patent
Shimizu et al.

(10) Patent No.: US 11,434,433 B2
(45) Date of Patent: Sep. 6, 2022

(54) COMPOSITION FOR REMOVAL OF SULFUR-CONTAINING COMPOUND

(71) Applicant: KURARAY CO., LTD., Kurashiki (JP)

(72) Inventors: Masaki Shimizu, Kamisu (JP); Yuusuke Saitou, Kamisu (JP); Takuo Tsuruta, Kamisu (JP)

(73) Assignee: KURARAY CO., LTD., Okayama (JP)

( * ) Notice: Subject to any disclaimer, the term of this patent is extended or adjusted under 35 U.S.C. 154(b) by 179 days.

(21) Appl. No.: 16/462,065

(22) PCT Filed: Nov. 20, 2017

(86) PCT No.: PCT/JP2017/041714
§ 371 (c)(1),
(2) Date: May 17, 2019

(87) PCT Pub. No.: WO2018/097108
PCT Pub. Date: May 31, 2018

(65) Prior Publication Data
US 2019/0330541 A1 Oct. 31, 2019

(30) Foreign Application Priority Data

Nov. 22, 2016 (JP) .............................. JP2016-226560
Jun. 21, 2017 (JP) .............................. JP2017-121287

(51) Int. Cl.
| | | |
|---|---|---|
| *C10G 29/20* | (2006.01) | |
| *B01D 53/14* | (2006.01) | |
| *C07C 7/11* | (2006.01) | |
| *C10C 3/08* | (2006.01) | |
| *C10L 3/10* | (2006.01) | |
| *C10L 10/02* | (2006.01) | |

(52) U.S. Cl.
CPC ......... *C10G 29/20* (2013.01); *B01D 53/1468* (2013.01); *B01D 53/1493* (2013.01); *C07C 7/11* (2013.01); *C10C 3/08* (2013.01); *C10L 3/103* (2013.01); *C10L 10/02* (2013.01); *B01D 2252/205* (2013.01); *B01D 2252/2041* (2013.01); *B01D 2252/20431* (2013.01); *B01D 2252/504* (2013.01); *C10G 2300/207* (2013.01); *C10L 2200/0263* (2013.01); *C10L 2290/542* (2013.01)

(58) Field of Classification Search
CPC .............. C10G 29/20; C10G 2300/207; B01D 53/1468; B01D 53/1493; B01D 2252/2041; B01D 2252/20431; B01D 2252/205; B01D 2252/504; B01D 2256/24; B01D 2257/304; B01D 2252/20415; B01D 53/14; C07C 7/11; C10C 3/08; C10L 3/103; C10L 10/02; C10L 2200/0263; C10L 2290/542

See application file for complete search history.

(56) References Cited

U.S. PATENT DOCUMENTS

| | | |
|---|---|---|
| 1,991,765 A | 2/1935 | Marks |
| 4,680,127 A | 7/1987 | Edmondson |
| 5,074,991 A | 12/1991 | Weers |
| 5,284,635 A | 2/1994 | Mabire |
| 5,698,171 A | 12/1997 | Trauffer et al. |
| 2009/0065445 A1 | 3/2009 | Westlund et al. |
| 2009/0145330 A1 | 6/2009 | Draper et al. |
| 2012/0216678 A1 | 8/2012 | Geuzebroek et al. |
| 2012/0329930 A1 | 12/2012 | Stark et al. |
| 2013/0004393 A1 | 1/2013 | Menendez et al. |
| 2013/0089460 A1 | 4/2013 | Keenan et al. |
| 2013/0090271 A1 | 4/2013 | Keenan et al. |
| 2018/0010056 A1 | 1/2018 | Suzuki et al. |

FOREIGN PATENT DOCUMENTS

| | | | |
|---|---|---|---|
| CA | 2974070 | * | 4/2016 |
| CN | 103619466 | | 3/2014 |
| GB | 461001 | * | 2/1937 |
| JP | 4-310213 A | | 11/1992 |
| JP | 2001-508349 A | | 6/2001 |
| JP | 2009-7479 A | | 1/2009 |
| JP | 2012-525964 A | | 10/2012 |
| JP | 2013-501608 A | | 1/2013 |
| JP | 2013-513718 A | | 4/2013 |
| JP | 2013-544305 A | | 12/2013 |
| JP | 2017-505866 A | | 2/2017 |
| KR | 20110120759 | | 11/2011 |
| WO | WO 2011/087540 A2 | | 7/2011 |
| WO | WO 2015/141535 A1 | | 9/2015 |
| WO | WO 2016/121747 A1 | | 8/2016 |

OTHER PUBLICATIONS

International Search Report dated Feb. 13, 2018 in PCT/JP2017/041714 filed Nov. 20, 2017.
Office Action issued in CN Patent Application No. 201780071174.9, dated Apr. 23, 2021.
Extended European Search Report issued in EP Patent Application No. 17874809.1, dated Apr. 24, 2020.

\* cited by examiner

*Primary Examiner* — Thuan D Dang
(74) *Attorney, Agent, or Firm* — Greenblum & Bernstein, P.L.C.

(57) ABSTRACT

Provided is a composition for removal of a sulfur-containing compound in a liquid or gas, wherein the sulfur-containing compound is at least one selected from the group consisting of hydrogen sulfide and a compound containing an —SH group, and the composition contains an aldehyde and a polyvalent amine represented by the general formula (1).

15 Claims, 1 Drawing Sheet

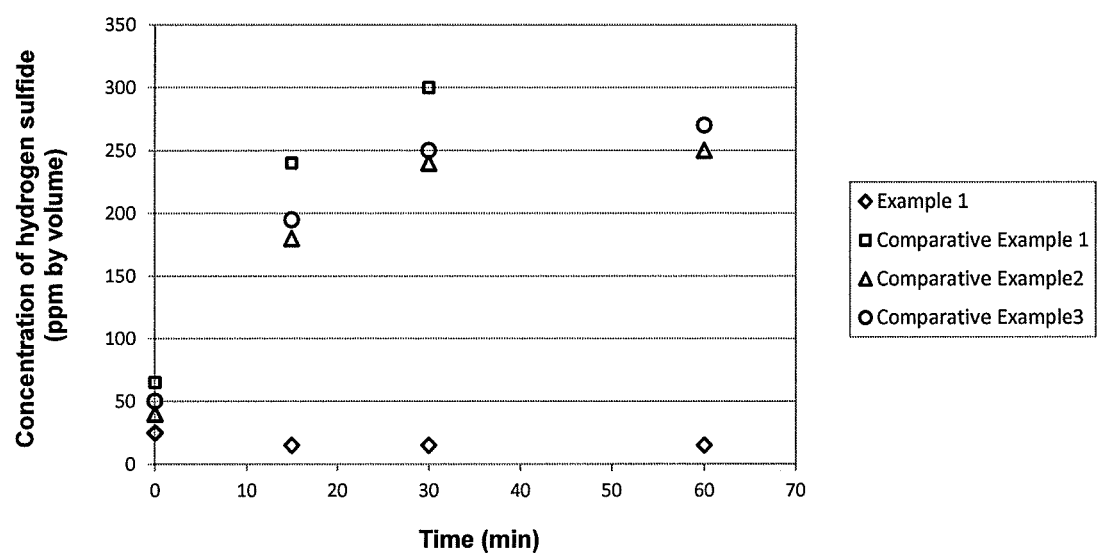

COMPOSITION FOR REMOVAL OF SULFUR-CONTAINING COMPOUND

FIELD OF THE INVENTION

The present invention relates to a composition for removal of a sulfur-containing compound in a liquid or gas.

BACKGROUND OF THE INVENTION

As a method for removing a sulfur-containing compound (in particular, hydrogen sulfide, a compound containing an —SH group, etc.) which is included in a liquid or gas and in which its toxicity, an offensive odor, or the like is regarded as a problem, a method in which an aldehyde, such as formaldehyde, glyoxal, glutaraldehyde, 3-methylglutaraldehyde, 1,9-nonanedial, and 2-methyl-1,8-octanedial, or a metal salt, such as zinc oxide, zinc sulfate, zinc carbonate, tetranuclear oxo zinc octoate, calcium oxide, calcium carbonate, and an amino acid metal chelate, is added to the system, thereby converting the sulfur-containing compound into a compound with a low odor or a compound with a low toxicity, and so on are known (see PTLs 1 to 14).

CITATION LIST

Patent Literature

PTL 1: U.S. Pat. No. 1,991,765 A
PTL 2: U.S. Pat. No. 4,680,127 A
PTL 3: U.S. Pat. No. 5,284,635 A
PTL 4: WO 2011/087540 A
PTL 5: JP 2012-525964 A
PTL 6: JP 2013-544305 A
PTL 7: US 2013/0090271 A
PTL 8: US 2013/0089460 A
PTL 9: WO 2015/141535 A
PTL 10: WO 2016/121747 A
PTL 11: US 2009/0145330 A
PTL 12: JP 2013-513718 A
PTL 13: JP 2009-007479 A
PTL 14: JP 2017-505866 A

SUMMARY OF THE INVENTION

Technical Problem

Although it is possible to remove a sulfur-containing compound included in a liquid or gas, particularly a sulfur-containing compound included in a hydrocarbon which is a liquid or gas by the aforementioned method, there is still room for improvement on the removal efficiency.

Solution to Problem

An object of the present invention is to provide a composition and a method, by which the sulfur-containing compound (at least one selected from the group consisting of hydrogen sulfide and a compound containing an —SH group) included in a liquid or gas can be efficiently removed.

The present inventors have found that as compared with the case of using an aldehyde alone, the sulfur-containing compound can be efficiently removed through a joint use of an aldehyde and a specified amine and further made extensive and intensive investigations on a basis of the foregoing finding, thereby leading to accomplishment of the present invention.

The present invention is concerned with the following [1] to [13].

[1] A composition for removal of a sulfur-containing compound in a liquid or gas, wherein the sulfur-containing compound is at least one selected from the group consisting of hydrogen sulfide and a compound containing an —SH group, and the composition contains an aldehyde and a polyvalent amine represented by the following general formula (1) (hereinafter sometimes referred to as "polyvalent amine (1)").

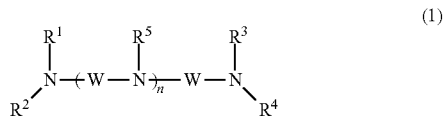

In the formula, W represents a methylene group, a dimethylene group, or a trimethylene group; $R^1$ to $R^5$ each independently represent a hydrogen atom, an alkyl group having 1 to 6 carbon atoms, an alkenyl group having 2 to 6 carbon atoms, an aralkyl group having 7 to 20 carbon atoms, or an aryl group having 6 to 12 carbon atoms, provided that $R^1$ and $R^2$ may be connected with each other to form a ring and $R^3$ and $R^4$ may be connected with each other to form a ring; n represents an integer of 0 to 3,000; W may be substituted with at least one $R^6$ (where $R^6$ represents an alkyl group having 1 to 6 carbon atoms, an alkenyl group having 2 to 6 carbon atoms, an aralkyl group having 7 to 20 carbon atoms, or an aryl group having 6 to 12 carbon atoms); $R^1$ to $R^6$ may be each substituted with a hydroxyl group or an alkoxy group having 1 to 6 carbon atoms; and in the case where a plurality of W are present, they are not necessarily the same group, in the case where a plurality of $R^5$ are present, they are not necessarily the same group, and in the case where a plurality of $R^6$ are present, they are not necessarily the same group.

[2] The composition as set forth in [1], wherein in the general formula (1), all of W are a dimethylene group.
[3] The composition as set forth in [1] or [2], wherein in the general formula (1), n is an integer of 0 to 5.
[4] The composition as set forth in any of [1] to [3], wherein the aldehyde is at least one selected from the group consisting of an α,β-unsaturated aldehyde and a dialdehyde.
[5] The composition as set forth in any of [1] to [3], wherein the aldehyde is at least one selected from the group consisting of acrolein, senecioaldehyde, glyoxal, glutaraldehyde, 3-methylglutaraldehyde, 1,9-nonanedial, and 2-methyl-1,8-octanedial.
[6] The composition as set forth in any of [1] to [5], wherein the liquid or gas is a hydrocarbon.
[7] The composition as set forth in any of [1] to [5], wherein the liquid or gas is at least one selected from the group consisting of natural gas, liquefied natural gas (LNG), liquefied petroleum gas (LPG), sour gas, dry gas, wet gas, oil field gas, associated gas, tail gas, dimethyl ether, crude oil, naphtha, heavy aromatic naphtha, gasoline, kerosene, diesel oil, light oil, lubricating oil, heavy oil, A-heavy oil, B-heavy oil, C-heavy oil, jet fuel oil, FCC slurry, asphalt, condensate, bitumen, extra heavy oil, tar, gas to liquid (GTL), coal to liquid (CTL), asphaltene, aromatic hydrocarbons, alkylates, base oil, kerogen, coke, black oil, synthetic crude oil, reformed gasoline, isomerate gasoline, regenerated heavy oil, residual oil, gasoline and distilled oil, raffinate, wax, biomass fuel, biomass to liquid (BTL), biogasoline, bioethanol, bio-ETBE, and biodiesel.

[8] A method for removal of a sulfur-containing compound in a liquid or gas, the method including bringing the composition as set forth in any of [1] to [7] into contact with the liquid or gas, the sulfur-containing compound being at least one selected from the group consisting of hydrogen sulfide and a compound containing an —SH group.

[9] The method as set forth in [8], wherein the composition is brought into contact with the liquid or gas such that the amount of the aldehyde included in the composition is 0.1 to 5,000 parts by mass based on 1 part by mass of the sulfur-containing compound included in the liquid or gas.

[10] The method as set forth in [8] or [9], wherein the composition is brought into contact with the liquid or gas at a temperature ranging from −30 to 500° C.

[11] Use of the composition as set forth in any of [1] to [7] for removal of a sulfur-containing compound in a liquid or gas, wherein the sulfur-containing compound is at least one selected from the group consisting of hydrogen sulfide and a compound containing an —SH group.

[12] A hydrocarbon containing the composition as set forth in any of [1] to [5].

[13] An asphalt containing the composition as set forth in any of [1] to [5].

The composition of the present invention is excellent in the removal efficiency of a sulfur-containing compound (at least one selected from the group consisting of hydrogen sulfide and a compound containing an —SH group) in a liquid or gas.

BRIEF DESCRIPTION OF THE DRAWINGS

FIG. 1 is a plot showing a change with time of a concentration of hydrogen sulfide in an exhaust in Example 1 and Comparative Examples 1 to 3.

DETAILED DESCRIPTION OF THE INVENTION

The composition of the present invention for removing a sulfur-containing compound in a liquid or gas contains an aldehyde and a polyvalent amine (1). Here, the sulfur-containing compound to be removed is at least one selected from the group consisting of hydrogen sulfide and a compound containing an —SH group.

The composition of the present invention is excellent in the removal efficiency of the sulfur-containing compound (at least one selected from the group consisting of hydrogen sulfide and a compound containing an —SH group) in the liquid or gas owing to the matter that it contains the aldehyde and the polyvalent amine (1) as active components. Although the reason why in the case of using the composition of the present invention, the removal efficiency is remarkably improved as compared with the related-art sulfur-containing compound removing agent containing an aldehyde is not entirely elucidated yet, the matter that on the occasion when the aldehyde and the sulfur-containing compound react with each other, the polyvalent amine is coordinated with an intermediate and stabilized, whereby a reaction rate is improved may be considered to be one factor.

The composition of the present invention is one for removing the sulfur-containing compound in the liquid or gas. In the present invention, the matter that for example, the sulfur-containing compound existent in the liquid or gas, which is to be removed, namely at least one selected from the group consisting of hydrogen sulfide and a compound containing an —SH group, is converted into another compound, thereby decreasing the initial amount of the foregoing sulfur-containing compound (at least one selected from the group consisting of hydrogen sulfide and a compound containing an —SH group) in the liquid or gas is to be included in the "removal". The converted product after conversion into another compound may be remained as it stands in the system, or may be separated outside the system.

Examples of a typical removal method include a method in which the composition of the present invention is brought into a liquid or gas including a sulfur-containing compound, and the composition after contact and the liquid or gas after contact are then separated from each other, resulting in decreasing the initial amount of the sulfur-containing compound in the liquid or gas, as described later.

<Composition>

[Liquid or Gas]

Although the liquid or gas which is subject to use the composition of the present invention is not particularly limited, examples thereof include water and a hydrocarbon, with a hydrocarbon being preferred.

Specific examples of the liquid or gas include natural gas, liquefied natural gas (LNG), liquefied petroleum gas (LPG), sour gas, dry gas, wet gas, oil field gas, associated gas, tail gas, dimethyl ether, crude oil, naphtha, heavy aromatic naphtha, gasoline, kerosene, diesel oil, light oil, lubricating oil, heavy oil, A-heavy oil, B-heavy oil, C-heavy oil, jet fuel oil, FCC slurry, asphalt, condensate, bitumen, extra heavy oil, tar, gas to liquid (GTL), coal to liquid (CTL), asphaltene, aromatic hydrocarbons, alkylates, base oil, kerogen, coke, black oil, synthetic crude oil, reformed gasoline, isomerate gasoline, regenerated heavy oil, residual oil, gasoline and distilled oil, raffinate, wax, biomass fuel, biomass to liquid (BTL), biogasoline, bioethanol, bio-ETBE (bio-ethyl tert-butyl ether), and biodiesel. The liquid or gas may be used either alone or in combination of two or more thereof.

As for the term "asphalt", though there may be a case where it refers to merely a heaviest component among hydrocarbons included in crude oil, or a case where it refers to a material for road pavement resulting from addition of various additives, etc. to the foregoing component, in the present specification, the "asphalt" is used as a generic term without distinguishing the both from each other.

Although the asphalt which is subject to use the composition of the present invention is not particularly limited, examples thereof include straight asphalt, solvent deasphalting asphalt, cutback asphalt, blown asphalt, catalytic blown asphalt, semiblown asphalt, rock asphalt, lake asphalt, oil sand, tar sand, oil shale, asphaltite, glance pitch, gilsonite, grahamite, and recycled asphalt. The asphalt may be used either alone or in combination of two or more thereof.

In addition, these asphalts may or may not include various additives.

Although the various additives which may be added to the asphalt are not particularly limited, examples thereof include sand or gravel, broken stone, stone dust, recycled aggregate, filler, fly ash, slag, rubber or polymer, sulfur, fibers, surfactant, corrosion inhibitor, oxygen scavenger, iron control agent, crosslinking agent, breaker, coagulant, temperature stabilizer, pH adjustor, dehydration modifier, swelling inhibitor, scale inhibitor, biocide, friction reducer, defoaming agent, lost circulation material, lubricant, clay dispersant, weighting agent, gelling agent, additive for recycled asphalt, mixing enhancer, compaction enhancer, emulsifier, asphalt emulsifier, and anti-stripping agent. These additives may be used either alone or in combination of two or more thereof.

[Sulfur-Containing Compound]

The sulfur-containing compound which is subject to the removal in the present invention is at least one selected from the group consisting of hydrogen sulfide and a compound containing an —SH group. That is, the subject to be removed may be only hydrogen sulfide or only the compound containing an —SH group, or may be a mixture of them.

The compound containing an —SH group is not particularly limited, and examples thereof include a sulfur-containing compound to be classified as a mercaptan represented by a chemical formula "R—SH". Examples of the mercaptan represented by the chemical formula "R—SH" include those in which R is an alkyl group, inclusive of methyl mercaptan, ethyl mercaptan, n-propyl mercaptan, isopropyl mercaptan, n-butyl mercaptan, isobutyl mercaptan, sec-butyl mercaptan, tert-butyl mercaptan, and n-amyl mercaptan; those in which R is an aryl group, inclusive of phenyl mercaptan; and those in which R is an aralkyl group, inclusive of benzyl mercaptan. The compound containing an —SH group which is subject to the removal may be used either alone or in combination of two or more thereof.

[Aldehyde]

The composition of the present invention contains an aldehyde.

The aldehyde which is used in the present invention is not particularly limited, and examples thereof include monoaldehydes, inclusive of formaldehyde, acetaldehyde, propionaldehyde, butanal, pentanal, hexanal, heptanal, octanal, nonanal, decanal, and benzaldehyde; α,β-unsaturated aldehydes, inclusive of acrolein and senecioaldehyde; and dialdehydes, inclusive of glyoxal, malondialdehyde, succinaldehyde, glutaraldehyde, 3-methylglutaraldehyde, 1,6-hexanedial, ethylpentanedial, 1,7-heptanedial, methylhexanedial, 1,8-octanedial, methylheptanedial, dimethylhexanedial, ethylhexanedial, 1,9-nonanedial, 2-methyl-1,8-octanedial, ethylheptanedial, 1,10-decanedial, dimethyloctanedial, ethyloctanedial, dodecanedial, hexadecanedial, 1,2-cyclohexane dicarboaldehyde, 1,3-cyclohexane dicarboaldehyde, 1,4-cyclohexane dicarboaldehyde, 1,2-cyclooctane dicarboaldehyde, 1,3-cyclooctane dicarboaldehyde, 1,4-cyclooctane dicarboaldehyde, and 1,5-cyclooctane dicarboaldehyde. The aldehyde may be used either alone or in combination of two or more thereof.

Above all, from the viewpoint of removal efficiency of the sulfur-containing compound, at least one compound selected from the group consisting of an α,β-unsaturated aldehyde and a dialdehyde is preferred, and at least one compound selected from the group consisting of acrolein, senecioaldehyde, glyoxal, glutaraldehyde, 3-methylglutaraldehyde, 1,9-nonanedial, and 2-methyl-1,8-octanedial is more preferred. From the viewpoints of low toxicity, biodegradability, safety on handling, heat resistance, low metal corrosiveness, and so on, at least one compound selected from the group consisting of senecioaldehyde, 1,9-nonanedial, and 2-methyl-1,8-octanedial is still more preferred.

From the viewpoint that the composition of the present invention is high in hydrophobicity and easily applicable to hydrocarbons, at least one compound selected from the group consisting of 1,9-nonanedial and 2-methyl-1,8-octanedial is preferred.

In view of the fact that the aldehyde reacts with the sulfur-containing compound, the sulfur-containing compound is removed from the liquid or gas. Although the mode of the reaction is not particularly limited, for example, in the case where the aldehyde is an α,β-unsaturated aldehyde, the sulfur-containing compound may undergo an addition reaction on a carbon-carbon double bond. In addition, in the case of other aldehyde, the sulfur-containing compound may undergo an addition reaction on a formyl group.

In the case of using at least one of 1,9-nonanedial and 2-methyl-1,8-octanedial as the aldehyde, though 1,9-nonanedial or 2-methyl-1,8-octanedial may be used alone, from the viewpoint of easiness of industrial availability, it is preferred to use 1,9-nonanedial and 2-methyl-1,8-octanedial as a mixture. Although a mixing ratio of the mixture of 1,9-nonanedial and 2-methyl-1,8-octanedial is not particularly limited, in general, a 1,9-nonanedial/2-methyl-1,8-octanedial mass ratio is preferably 99/1 to 1/99, more preferably 95/5 to 5/95, still more preferably 93/7 to 45/55, and especially preferably 90/10 to 55/45.

[Polyvalent Amine]

The composition of the present invention contains a polyvalent amine (1).

The polyvalent amine (1) which is used in the present invention is represented by the following general formula (1).

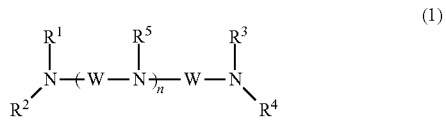

In the general formula (1), W represents a methylene group, a dimethylene group, or a trimethylene group; $R^1$ to $R^5$ each independently represent a hydrogen atom, an alkyl group having 1 to 6 carbon atoms, an alkenyl group having 2 to 6 carbon atoms, an aralkyl group having 7 to 20 carbon atoms, or an aryl group having 6 to 12 carbon atoms, provided that $R^4$ and $R^2$ may be connected with each other to form a ring and $R^3$ and $R^4$ may be connected with each other to form a ring (namely, the polyvalent amine (1) may have only a ring formed by $R^1$ and $R^2$ which are connected with each other, only a ring formed by $R^3$ and $R^4$ which are connected with each other, or both a ring formed by $R^4$ and $R^2$ and a ring formed by $R^3$ and $R^4$); n represents an integer of 0 to 3,000; W may be substituted with at least one $R^6$ (namely, at least one hydrogen atom included in W may be substituted with $R^6$, where $R^6$ represents an alkyl group having 1 to 6 carbon atoms, an alkenyl group having 2 to 6 carbon atoms, an aralkyl group having 7 to 20 carbon atoms, or an aryl group having 6 to 12 carbon atoms); W to $R^6$ may be each substituted with a hydroxyl group or an alkoxy group having 1 to 6 carbon atoms (namely, at least one hydrogen atom included in each of $R^1$ to $R^6$ may be substituted with a hydroxy group or an alkoxy group having 1 to 6 carbon atoms); and in the case where a plurality of W are present, they are not necessarily the same group, in the case where a plurality of $R^5$, they are not necessarily the same group, and in the case where a plurality of $R^6$ are present, they are not necessarily the same group.

In the polyvalent amine (1), W is preferably a dimethylene group or a trimethylene group, and more preferably a dimethylene group. It is especially preferred that all of W in the general formula (1) are a dimethylene group.

$R^1$ to $R^5$ are each preferably a hydrogen atom or an alkyl group having 1 to 6 carbon atoms, more preferably a hydrogen atom or an alkyl group having 1 to 4 carbon atoms, and still more preferably a hydrogen atom or a methyl group.

n is preferably an integer of 0 to 1,000, more preferably an integer of 0 to 100, still more preferably an integer of 0 to 10, and especially preferably an integer of 0 to 5.

Examples of the polyvalent amine (1) in which n is 0 include:

compounds in which W is a methylene group, inclusive of N,N,N',N'-tetramethyldiaminomethane;

compounds in which W is a dimethylene group, inclusive of ethylenediamine, 1,2-diaminopropane, 1,2-diamino-2-methylpropane, N-methylethylenediamine, N-ethylethylenediamine, N-propylethylenediamine, N-butylethylenediamine, N-benzylethylenediamine, N-phenylethylenediamine, N,N-dimethylethylenediamine, N,N-diethylethylenediamine, N,N-dipropylethylenediamine, N,N-dibutylethylenediamine, N,N'-dimethylethylenediamine, N,N'-diethylethylenediamine, N,N'-dipropylethylenediamine, N,N'-diisopropylethylenediamine, N,N'-di-tert-butylethylenediamine, N,N'-dibenzylethylenediamine, N,N'-diphenylethylenediamine, N,N'-bis(2-hydroxyethyl)ethylenediamine, N,N,N'-trimethylethylenediamine, N,N,N'-triethylethylenediamine, N,N-diethyl-N'-methylethylenediamine, N,N,N',N'-tetramethylethylenediamine, N,N,N',N'-tetraethylethylenediamine, N,N,N',N'-tetraisopropylethylenediamine, and N,N,N',N'-tetramethyl-1,2-diaminopropane; and compounds in which W is a trimethylene group, inclusive of 1,3-propanediamine, 2-methyl-1,3-propanediamine, 1,3-diaminobutane, 2,2-dimethyl-1,3-propane diamine, 1,3-diaminopentane, N-methyl-1,3-propanediamine, N-ethyl-1,3-propanediamine, N-propyl-1,3-propanediamine, N-butyl-1,3-propanediamine, N-benzyl-1,3-propanediamine, N-phenyl-1,3-propanediamine, N,N-dimethyl-1,3-propanediamine, N,N-diethyl-1,3-propanediamine, N,N-dipropyl-1,3-propanediamine, N,N'-dimethyl-1,3-propanediamine, N,N'-diethyl-1,3-propanediamine, N,N,N'-trimethyl-1,3-propanediamine, N,N,N',N'-tetramethyl-1,3-propanediamine, N,2-dimethyl-1,3-propanediamine, and N,N,2,2-tetramethyl-1,3-propanediamine.

Examples of the polyvalent amine (1) in which n is 1 include:

compounds in which W is a dimethylene group, inclusive of diethylenetriamine, 2,2'-diamino-N-methyldiethylamine, N,N',N''-trimethyldiethylenetriamine, N,N,N',N'',N''-pentamethyldiethylenetriamine, and N,N,N',N'-tetrabutyldiethylenetriamine; and compounds in which W is a trimethylene group, inclusive of 3,3'-diaminodipropylamine and N,N-bis[3-(dimethylamino)propyl]amine.

Examples of the polyvalent amine (1) in which n is 2 or more include compounds in which n is 2, inclusive of triethylenetetramine and 1,1,4,7,10,10-hexamethyltriethylenetetramine; compounds in which n is 3, inclusive of tetraethylenepentamine; and compounds in which n is 4, inclusive of pentaethylenehexamine.

Above all, from the viewpoints of easiness of availability and effect for removing the sulfur-containing compound, ethylenediamine, N-methylethylenediamine, N,N-dimethylethylenediamine, N,N'-dimethylethylenediamine, N,N,N'-trimethylethylenediamine, N,N,N',N'-tetramethylethylenediamine, diethylenetriamine, 2,2'-diamino-N-methyldiethylamine, N,N,N',N'',N''-pentamethyldiethylenetriamine, and triethylenetetramine are preferred; and ethylenediamine, N-methylethylenediamine, N,N-dimethylethylenediamine, N,N'-dimethylethylenediamine, N,N,N'-trimethylethylenediamine, N,N,N',N'-tetramethylethylenediamine, and diethylenetriamine are more preferred.

The polyvalent amine (1) may be used either alone or in combination of two or more thereof.

The polyvalent amine (1) to be used may be a commercially available product, or may be produced by a known method, for example, a reaction between ammonia and an alkyl halide.

[Contents]

A sum total of the contents of the aldehyde and the polyvalent amine (1) in the composition of the present invention can be properly set according to a use mode. The sum total of the contents may be 0.1% by mass or more, may be 10% by mass or more, may be 30% by mass or more, may be 50% by mass or more, may be 80% by mass or more, and may be 100% by mass. In the case where the aldehyde and the polyvalent amine (1) are used upon being diluted with a solvent, the sum total of the contents may be 90% by mass or less, may be 60% by mass or less, may be 30% by mass or less, and may be 5% by mass or less.

As for a ratio of the contents of the aldehyde and the polyvalent amine (1) in the composition of the present invention, in the case of defining the aldehyde as A (parts by mass) and the polyvalent amine (1) as B (parts by mass), respectively, the A/B ratio is typically 0.1/99.9 to 99.9/0.1, and from the viewpoint of cost-effectiveness, the A/B ratio is preferably 20/80 to 99.5/0.5, and more preferably 40/60 to 99/1.

[Arbitrary Components]

So long as the effects of the present invention are not impaired, the composition of the present invention may further include, in addition to the aldehyde and the polyvalent amine (1), an arbitrary component, such as a surfactant, a corrosion inhibitor, an oxygen scavenger, an iron control agent, a crosslinking agent, a breaker, a coagulant, a temperature stabilizer, a pH adjustor, a dehydration modifier, a swelling inhibitor, a scale inhibitor, a biocide, a friction reducer, a defoaming agent, a lost circulation material, a lubricant, a clay dispersant, a weighting agent, a gelling agent, and a nitrogen-containing compound other than the polyvalent amine (1).

The composition of the present invention may also include, as an arbitrary component, a suitable solvent, such as a monoalcohol or diol having 1 to 10 carbon atoms, inclusive of methanol, ethanol, 2-propanol, and ethylene glycol, cyclohexane, toluene, xylene, a heavy aromatic naphtha, a petroleum distillate, and water.

[Method of Producing the Composition]

A production method of the composition of the present invention is not particularly limited. The composition of the present invention can be produced through mixing of the aldehyde and the polyvalent amine (1) and optionally, an arbitrary component, for example, a method in which the polyvalent amine (1) is added to the aldehyde, and an arbitrary component, such as the aforementioned solvent, is further added thereto and mixed therewith.

Although the composition of the present invention is suitably in a liquid state, it may be properly supported on a carrier or the like and formed in a solid, such as a powder and a granule according to a use mode for removing the sulfur-containing compound in the liquid or gas.

[Method of Removing the Sulfur-Containing Compound]

In removing the sulfur-containing compound (at least one selected from the group consisting of hydrogen sulfide and a compound containing an —SH group) in the liquid or gas with the composition of the present invention, the composition of the present invention may be brought into contact with the liquid or gas.

Examples of a preferred, specific embodiment according to the removal method of the sulfur-containing compound include a method in which the composition of the present invention in a sufficient amount for removing the sulfur-containing compound is added to the liquid or gas; a method in which a gas (for example, a hydrocarbon) including the sulfur-containing compound is circulated into a vessel having the composition of the present invention filled therein; and a method in which the composition of the present invention is injected in a mist form into a gas including the sulfur-containing compound.

In removing the sulfur-containing compound in the liquid or gas with the composition of the present invention, the composition of the present invention and the liquid or gas may be brought into contact with each other in such a manner that the amount of the aldehyde included in the composition of the present invention is preferably 0.1 to 5,000 parts by mass, and more preferably 2 to 1,000 parts by mass based on 1 part by mass of the sulfur-containing compound included in the liquid or gas.

As described above, in the method in which the gas including the sulfur-containing compound is circulated into a vessel having the composition of the present invention filled therein, the use amount of the composition of the present invention may be adjusted in such a manner that the amount of the aldehyde to be used falls within the aforementioned range based on 1 part by mass of the sulfur-containing compound in the whole amount of the gas to be circulated.

Although the temperature at which the composition of the present invention and the liquid or gas are brought into contact with each other is not particularly limited, it is preferably in a range of from −30 to 500° C., and more preferably in a range of from 0 to 300° C. There may be a case where the temperature is preferably in a range of from −30 to 150° C., and more preferably in a range of from 0 to 130° C. depending upon an application.

After bringing the composition of the present invention and the liquid or gas into contact with each other, the composition after contact and the liquid or gas after contact may be separated from each other, as the need arises. In particular, such a separation method can also be adopted in the case where the composition after contact and the gas after contact can be easily separated from each other as in the aforementioned method in which a gas (for example, a hydrocarbon) including a sulfur-containing compound is circulated into a vessel having the composition of the present invention filled therein, or in the case where even in the case of removing the sulfur-containing compound in the liquid, phase separation between the composition after contact and the liquid after contact can be performed. In this way, not only the initial amount of the sulfur-containing compound in the liquid or gas can be decreased, but also the initial quality of the liquid or gas is more easily kept.

Furthermore, a mode in which the composition after contact and the gas or liquid after contact are not separated from each other may be considered, too. For example, in the case where there is no problem even when the hydrocarbon containing the composition of the present invention, or the asphalt containing the composition of the present invention, is used as it is in the subsequent step, it is possible to save time for the separation. Namely, the present invention also provides a hydrocarbon containing the composition of the present invention and an asphalt containing the composition of the present invention.

As a more specific mode in removing the sulfur-containing compound in the liquid or gas with the composition of the present invention, the following can be exemplified.

That is, in removing the sulfur-containing compound in water with the composition of the present invention, for example, a means for injecting the composition of the present invention into a water tank in a sewage treatment plant, or the like can be adopted.

In removing the sulfur-containing compound in the hydrocarbon with the composition of the present invention, in the case where the hydrocarbon is a liquid, the composition can be added by a known means, such as injection into a storage tank thereof, a pipe line for transportation, a distillation tower for refinement, or the like. In the case where the hydrocarbon is a gas, a means of placing the composition of the present invention so as to bring it into contact with the gas as described above, or allowing the gas through an absorption tower having the composition of the present invention filled therein, can be taken.

EXAMPLES

The present invention is hereunder described in more detail by reference to Examples and so on, but it should be construed that the present invention is by no means limited by these Examples.

Production Example 1

[Production of Mixture of 1,9-nonanedial (NL) and 2-methyl-1,8-octanedial (MOL)]

A mixture of 1,9-nonanedial (hereinafter referred to as NL) and 2-methyl-1,8-octanedial (hereinafter referred to as MOL) (this mixture will be hereinafter referred to as NL/MOL) was produced by a method described in Japanese Patent No. 2857055. A mass ratio of NL and MOL in the mixture was NL/MOL=85/15.

[Production of Senecioaldehyde (SAL)]

Senecioaldehyde (hereinafter referred to as SAL) was produced from prenol by a method described in JP 60-224652 A (purity: 98.1% by mass).

Example 1

Into a 500-mL trap flask, a mixed gas composed of a composition of 1% by volume of hydrogen sulfide and 99% by volume of nitrogen and a gas of 100% by volume of methane were circulated at a flow rate of 10 mL/min and 320 mL/min, respectively, followed by purging the inside of the flask. After thoroughly purging, the concentration of hydrogen sulfide in an exhaust was measured by a Kitagawa gas detector tube system (used by installing a hydrogen sulfide detector tube, manufactured by Komyo Rikagaku Kogyo K.K. in a gas aspirating pump "AP-20") and found to be 300 ppm by volume. Subsequently, 250 g of a separately prepared solution of 5,000 ppm of NL/MOL and 2,500 ppm of N,N,N',N'-tetramethylethylenediamine (manufactured by Wako Pure Chemical Industries, Ltd.) in 2-propanol (manufactured by Wako Pure Chemical Industries, Ltd.) was charged in the flask. The concentration of hydrogen sulfide in the exhaust was measured after a lapse of 0 minute, 15 minutes, 30 minutes, and 60 minutes, respectively while defining a lapse of time immediately after charging as 0 minute. The results are shown in Table 1 and FIG. 1.

Comparative Example 1

The same operations as in Example 1 were followed, except for changing the 2-propanol solution (250 g) of 5,000 ppm of NL/MOL and 2,500 ppm of N,N,N',N'-tetramethylethylenediamine to 250 g of 2-propanol. The results are shown in Table 1 and FIG. 1.

Comparative Example 2

The same operations as in Example 1 were followed, except for changing the 2-propanol solution (250 g) of 5,000 ppm of NL/MOL and 2,500 ppm of N,N,N',N'-tetramethylethylenediamine to 250 g of a 2-propanol solution of 5,000 ppm of NL/MOL. The results are shown in Table 1 and FIG. 1.

Comparative Example 3

The same operations as in Example 1 were followed, except for changing the 2-propanol solution (250 g) of 5,000 ppm of NL/MOL and 2,500 ppm of N,N,N',N'-tetramethylethylenediamine to 250 g of a 2-propanol solution of 2,500 ppm of N,N,N',N'-tetramethylethylenediamine. The results are shown in Table 1 and FIG. 1.

TABLE 1

| | Concentration of hydrogen sulfide [ppm by volume] | | | | |
|---|---|---|---|---|---|
| | Initial | 0 min | 15 min | 30 min | 60 min |
| Example 1 | 300 | 25 | 15 | 15 | 15 |
| Comparative Example 1 | | 65 | 240 | 300 | — |
| Comparative Example 2 | | 40 | 180 | 240 | 250 |
| Comparative Example 3 | | 50 | 195 | 250 | 270 |

From Example 1 and Comparative Examples 1 to 3, it is noted that when the aldehyde and the polyvalent amine (1) are allowed to coexist, the removal efficiency of hydrogen sulfide is improved.

Example 2

The same operations as in Example 1 were followed, except for changing the 2-propanol solution (250 g) of 5,000 ppm of NL/MOL and 2,500 ppm of N,N,N',N'-tetramethylethylenediamine to 250 g of a 2-propanol solution of 1,000 ppm of NL/MOL and 500 ppm of N,N,N',N'-tetramethylethylenediamine. The results are shown in Table 2.

Example 3

The same operations as in Example 1 were followed, except for changing the 2-propanol solution (250 g) of 5,000 ppm of NL/MOL and 2,500 ppm of N,N,N',N'-tetramethylethylenediamine to 250 g of a 2-propanol solution of 10,000 ppm of NL/MOL and 500 ppm of N,N,N',N'-tetramethylethylenediamine. The results are shown in Table 2.

TABLE 2

| | Concentration of hydrogen sulfide [ppm by volume] | | | | |
|---|---|---|---|---|---|
| | Initial | 0 min | 15 min | 30 min | 60 min |
| Example 2 | 300 | 45 | 70 | 75 | 75 |
| Example 3 | | 30 | 45 | 55 | 60 |

Example 4

The same operations as in Example 1 were followed, except for changing the N,N,N',N'-tetramethylethylenediamine to ethylenediamine (manufactured by Wako Pure Chemical Industries, Ltd.). The results are shown in Table 3.

Example 5

The same operations as in Example 1 were followed, except for changing the N,N,N',N'-tetramethylethylenediamine to N,N,N',N'-tetramethyl-1,3-propanediamine (manufactured by Wako Pure Chemical Industries, Ltd.). The results are shown in Table 3.

Example 6

The same operations as in Example 1 were followed, except for changing the N,N,N',N'-tetramethylethylenediamine to pentaethylenehexamine (manufactured by Wako Pure Chemical Industries, Ltd.). The results are shown in Table 3.

TABLE 3

| | Concentration of hydrogen sulfide [ppm by volume] | | | | |
|---|---|---|---|---|---|
| | Initial | 0 min | 15 min | 30 min | 60 min |
| Example 4 | 300 | 80 | 30 | 30 | 40 |
| Example 5 | | 110 | 45 | 60 | 70 |
| Example 6 | | 100 | 40 | 50 | 60 |

From Examples 4 to 6, it could be confirmed that even the primary diamine, the diamine in which the carbon number between the nitrogen atoms is 3, and the polyvalent amine having the nitrogen number of 6 are effective for improving the removal efficiency of hydrogen sulfide.

Example 7

The same operations as in Example 1 were followed, except for changing the NL/MOL and the 2-propanol solution to glyoxal (manufactured by Tokyo Chemical Industry Co., Ltd.) and an aqueous solution, respectively. The results are shown in Table 4.

Example 8

The same operations as in Example 1 were followed, except for changing the NL/MOL and the 2-propanol solution to glutaraldehyde (manufactured by Tokyo Chemical Industry Co., Ltd.) and an aqueous solution, respectively. The results are shown in Table 4.

TABLE 4

| | Concentration of hydrogen sulfide [ppm by volume] | | | | |
|---|---|---|---|---|---|
| | Initial | 0 min | 15 min | 30 min | 60 min |
| Example 7 | 300 | 20 | 15 | 15 | 15 |
| Example 8 | | 20 | 15 | 20 | 20 |

Example 9

The same operations as in Example 1 were followed, except for changing the NL/MOL to acrolein (manufactured by Tokyo Chemical Industry Co., Ltd.). The results are shown in Table 5.

Comparative Example 4

The same operations as in Example 1 were followed, except for changing the 2-propanol solution (250 g) of 5,000 ppm of NL/MOL and 2,500 ppm of N,N,N',N'-tetramethylethylenediamine to 250 g of a 2-propanol solution of 5,000 ppm of acrolein. The results are shown in Table 5.

Example 10

The same operations as in Example 1 were followed, except for changing the NL/MOL to SAL. The results are shown in Table 5.

Comparative Example 5

The same operations as in Example 1 were followed, except for changing the 2-propanol solution (250 g) of 5,000 ppm of NL/MOL and 2,500 ppm of N,N,N',N'-tetramethylethylenediamine to 250 g of a 2-propanol solution of 5,000 ppm of SAL. The results are shown in Table 5.

TABLE 5

| | Concentration of hydrogen sulfide [ppm by volume] | | | | |
|---|---|---|---|---|---|
| | Initial | 0 min | 15 min | 30 min | 60 min |
| Example 9 | 300 | 40 | 60 | 70 | 90 |
| Comparative Example 4 | | 70 | 200 | 270 | — |
| Example 10 | 300 | 40 | 60 | 70 | 90 |
| Comparative Example 5 | | 50 | 150 | 240 | 270 |

From Examples 9 and 10 and Comparative Examples 4 and 5, it became clear that even the α,β-unsaturated aldehyde exhibits the same effects.

Comparative Example 6

The same operations as in Example 2 were followed, except for changing the N,N,N',N'-tetramethylethylenediamine to 1,2-cyclohexanediamine (manufactured by Tokyo Chemical Industry Co., Ltd.). The results are shown in Table 6.

Comparative Example 7

The same operations as in Example 2 were followed, except for changing the N,N,N',N'-tetramethylethylenediamine to 1,4-butanediamine (manufactured by Wako Pure Chemical Industries, Ltd.). The results are shown in Table 6.

Comparative Example 8

The same operations as in Example 2 were followed, except for changing the N,N,N',N'-tetramethylethylenediamine to N,N,N',N'-tetramethyl-1,4-butanediamine (manufactured by Tokyo Chemical Industry Co., Ltd.). The results are shown in Table 6.

Comparative Example 9

The same operations as in Example 2 were followed, except for changing the N,N,N',N'-tetramethylethylenediamine to 1,2-bis(2-aminoethoxy)ethane (manufactured by Tokyo Chemical Industry Co., Ltd.). The results are shown in Table 6

TABLE 6

| | Concentration of hydrogen sulfide [ppm by volume] | | | | |
|---|---|---|---|---|---|
| | Initial | 0 min | 15 min | 30 min | 60 min |
| Example 2 | 300 | 45 | 70 | 75 | 75 |
| Comparative Example 6 | 300 | 50 | 85 | 125 | 160 |
| Comparative Example 7 | 300 | 70 | 150 | 220 | 260 |
| Comparative Example 8 | 300 | 60 | 155 | 240 | 280 |
| Comparative Example 9 | 300 | 50 | 120 | 180 | 220 |

From Example 2 and Comparative Examples 6 to 9, it became clear that the polyvalent amine that is not the polyvalent amine (1) represented by the general formula (1) described above does not sufficiently exhibit the effects.

Example 11

A 110-mL sample bottle equipped with a magnetic stirrer and a rubber stopper installed with a gas distribution pipe was charged with 20 g of asphalt (a trade name: STRAIGHT ASPHALT 60/80, manufactured by Showa Shell Sekiyu K.K.). This sample bottle was heated at 120° C. by an oil bath, and a mixed gas composed of 1% by volume of hydrogen sulfide and 99% by volume of nitrogen was circulated in the sample bottle at a flow rate of 20 to 30 mL/min in a state of being subjected to magnetic stirring at a rotation rate of 400 rpm, thereby absorbing the hydrogen sulfide on the asphalt. After a lapse of 1.5 hours, the circulation of hydrogen sulfide was stopped, the concentration of hydrogen fluoride in a space part was measured in terms of an initial concentration of hydrogen sulfide by a Kitagawa gas detector tube system (used by installing a hydrogen sulfide detector tube, manufactured by Komyo Rikagaku Kogyo K.K. in a gas aspirating pump "AP-20"). Subsequently, a separately prepared mixture (sum total: 2,500 ppm) of mg (1,250 ppm) of NL/MOL and 25 mg (1,250 ppm) of N,N,N',N'-tetramethylethylenediamine (manufactured by Wako Pure Chemical Industries, Ltd.) was charged in the sample bottle. While continuing heating by the oil bath at 120° C. and magnetic stirring at 400 rpm, the concentration of hydrogen sulfide in the space part of the sample bottle was properly measured while defining the time of charging the mixture of NL/MOL and N,N,N',N'-tetramethylethylenediamine as 0 hour. The results are shown in Table 7. Since the concentration of hydrogen sulfide in the space part decreases with a decrease of the concentration of hydrogen sulfide in the asphalt, a change with time of the concentration of hydrogen sulfide in the asphalt can be indirectly known according to this measurement.

Comparative Example 10

The same operations as in Example 11 were followed, except for changing the mixture (sum total: 2,500 ppm) of 25 mg (1,250 ppm) of NL/MOL and 25 mg (1,250 ppm) of N,N,N',N'-tetramethylethylenediamine to 200 mg (10,000 ppm) of NL/MOL. The results are shown in Table 7.

Comparative Example 11

The same operations as in Example 11 were followed, except for changing the mixture (sum total: 2,500 ppm) of 25 mg (1,250 ppm) of NL/MOL and 25 mg (1,250 ppm) of N,N,N',N'-tetramethylethylenediamine to 50 mg (2,500 ppm) of zinc oxide (manufactured by Wako Pure Chemical Industries, Ltd.). The results are shown in Table 7.

Example 12

The same operations as in Example 11 were followed, except for changing the heating temperature by the oil bath from 120° C. to 200° C. The results are shown in Table 7.

Comparative Example 12

The same operations as in Example 12 were followed, except for changing the mixture (sum total: 2,500 ppm) of 25 mg (1,250 ppm) of NL/MOL and 25 mg (1,250 ppm) of N,N,N',N'-tetramethylethylenediamine to 50 mg (2,500 ppm) of zinc oxide (manufactured by Wako Pure Chemical Industries, Ltd.). The results are shown in Table 7.

TABLE 7

| | Concentration of hydrogen sulfide [ppm by volume] | | | | | | | |
|---|---|---|---|---|---|---|---|---|
| | 0 h | 0.5 h | 1 h | 1.5 h | 2 h | 3 h | 4 h | 6 h |
| Example 11 | 7800 | 2250 | 810 | — | 120 | 0 | 0 | 0 |
| Comparative Example 10 | 8700 | — | 2850 | — | 1200 | 300 | 120 | 30 |
| Comparative Example 11 | 8100 | 3000 | 2400 | — | 1280 | 600 | 240 | 30 |
| Example 12 | 6600 | 0 | 0 | 0 | — | — | — | — |
| Comparative Example 12 | 6600 | 900 | 120 | 0 | — | — | — | — |

From Examples 11 and 12 and Comparative Examples 10 to 12, it is noted that even in the case where the composition of the present invention is used for the asphalt, it is excellent in the efficiency of removal of hydrogen sulfide.

INDUSTRIAL APPLICABILITY

The composition of the present invention is useful from the standpoint that it is able to efficiently remove a sulfur-containing compound in which its toxicity, an offensive odor, or the like is regarded as a problem, from a liquid or gas.

The invention claimed is:
1. A composition, comprising:
an aldehyde which is at least one selected from the group consisting of an α,β-unsaturated aldehyde and a dialdehyde, and
a polyvalent amine of formula (1):

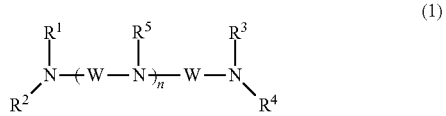

(1)

wherein W represents a methylene group, a dimethylene group, or a trimethylene group; $R^1$ to $R^4$ each independently represent a hydrogen, atom or an alkyl group having 1 to 6 carbon; $R^5$ represents a hydrogen atom or a methyl group; n represents an integer of 0 to 5; W is optionally substituted with at least one $R^6$, where $R^6$ represents an alkyl group having 1 to 6 carbon atoms, an alkenyl group having 2 to 6 carbon atoms, an aralkyl group having 7 to 20 carbon atoms, or an aryl group having 6 to 12 carbon atoms; $R^1$ to $R^6$ are each optionally substituted with a hydroxyl group or an alkoxy group having 1 to 6 carbon atoms; and in the case where a plurality of any W, $R^5$, and $R^6$ are present, the plurality of any W, $R^5$, and $R^6$ are optionally the same or different from each other.

2. The composition according to claim 1, wherein all of W are a dimethylene group.

3. The composition according to claim 1, wherein the aldehyde is at least one selected from the group consisting of acrolein; senecioaldehyde; glyoxal; glutaraldehyde; 3-methylglutaraldehyde; 1,9-nonanedial; and 2-methyl-1,8-octanedial.

4. A method for removal of a sulfur-containing compound in a liquid or gas, the method comprising:
bringing the composition according to claim 1 into contact with the liquid or gas,
wherein the sulfur-containing compound is at least one selected from the group consisting of hydrogen sulfide and a compound containing an -SH group.

5. The method according to claim 4, wherein the liquid or gas is a hydrocarbon.

6. The method according to claim 4, wherein the liquid or gas is at least one selected from the group consisting of natural gas, liquefied natural gas, liquefied petroleum gas, sour gas, dry gas, wet gas, oil field gas, associated gas, tail gas, dimethyl ether, crude oil, naphtha, heavy aromatic naphtha, gasoline, kerosene, diesel oil, light oil, lubricating oil, heavy oil, A-heavy oil, B-heavy oil, C-heavy oil, jet fuel oil, FCC slurry, asphalt, condensate, bitumen, extra heavy oil, tar, gas to liquid, coal to liquid, asphaltene, aromatic hydrocarbons, alkylates, base oil, kerogen, coke, black oil, synthetic crude oil, reformed gasoline, isomerate gasoline, regenerated heavy oil, residual oil, gasoline and distilled oil, raffinate, wax, biomass fuel, biomass to liquid, biogasoline, bioethanol, bio-ETBE, and biodiesel.

7. The method according to claim 4, wherein the composition is brought into contact with the liquid or gas such that an amount of the aldehyde included in the composition is from 0.1 to 5,000 parts by mass based on 1 part by mass of the sulfur-containing compound in the liquid or gas.

8. The method according to claim 4, wherein the composition is brought into contact with the liquid or gas at a temperature ranging from −30 to 500° C.

9. A composition comprising a hydrocarbon and the composition according to claim 1.

10. A composition comprising an asphalt and the composition according to claim 1.

11. The composition according to claim 1, wherein W represents a methylene group, a dimethylene group, or a trimethylene group; $R^1$ to $R^4$ each independently represent a hydrogen atom, atom or an alkyl group having 1 to 6 carbon atoms; $R^5$ represents a hydrogen atom or a methyl group; n represents an integer of 0 to 5; and in the case where a plurality of any W, and $R^5$ are present, the plurality of any W, and $R^5$ are optionally the same or different from each other.

12. The composition according to claim 11, wherein the aldehyde is at least one selected from the group consisting of acrolein; senecioaldehyde; glyoxal; malondialdehyde; succinaldehyde; glutaraldehyde; 3-methylglutaraldehyde; 1,6-hexanedial; ethylpentanedial; 1,7-heptanedial; methylhexanedial; 1,8-octanedial; methylheptanedial; dimethylhexanedial; ethylhexanedial; 1,9-nonanedial; 2-methyl-1,8-octanedial; ethylheptanedial; 1,10-decanedial; dimethyloctanedial; ethyloctanedial; dodecanedial; hexadecanedial; 1,2-cyclohexane dicarboaldehyde; 1,3-cyclohexane dicarboaldehyde; 1,4-cyclohexane dicarboaldehyde; 1,2-cyclooctane dicarboaldehyde; 1,3-cyclooctane dicarboaldehyde; 1,4-cyclooctane dicarboaldehyde; and 1,5-cyclooctane dicarboaldehyde.

13. The composition according to claim 1, wherein the polyvalent amine is at least one selected from the group consisting of N,N,N',N'-tetramethyldiaminomethane; ethylenediamine; 1,2-diaminopropane; 1,2-diamino-2-methylpropane; N-methylethylenediamine; N-ethylethylenediamine; N-propylethylenediamine; N-butylethylenediamine; N,N-dimethylethylenediamine; N,N-diethylethylenediamine; N,N-dipropylethylenediamine; N,N-dibutylethylenediamine; N,N'-dimethylethylenediamine; N,N'-diethylethylenediamine; N,N'-dipropylethylenediamine; N,N'-diisopropylethylenediamine; N,N'-di-tert-butylethylenediamine; N,N,N'-trimethylethylenediamine; N,N,N'-triethylethylenediamine; N,N-diethyl-N'-methylethylenediamine; N,N,N',N'-tetramethylethylenediamine; N,N,N',N'-tetraethylethylenediamine; N,N,N',N'-tetraisopropylethylenediamine; N,N,N',N'-tetramethyl-1,2-diaminopropane; 1,3-propanediamine; 2-methyl-1,3-propanediamine; 1,3-diaminobutane; 2,2-dimethyl-1,3-propanediamine; 1,3-diaminopentane; N-methyl-1,3-propanediamine; N-ethyl-1,3-propanediamine; N-propyl-1,3-propanediamine; N-butyl-1,3-propanediamine; N,N-dimethyl-1,3-propanediamine; N,N-diethyl-1,3-propanediamine; N,N-dipropyl-1,3-propanediamine; N,N'-dimethyl-1,3-propanediamine; N,N'-diethyl-1,3-propanediamine; N,N,N'-trimethyl-1,3-propanediamine; N,N,N',N'-tetramethyl-1,3-propanediamine; N,2-dimethyl-1,3-propanediamine; N,N,2,2-tetramethyl-1,3-propanediamine; diethylenetriamine; 2,2'-diamino-N-methyldiethylamine; N,N',N''-trimethyldiethylenetriamine; N,N,N',N'',N''-pentamethyldiethylenetriamine; 3,3'-diaminodipropylamine; N,N-bis[3-(dimethylamino)propyl]amine; triethylenetetramine; 1,1,4,7,10,10-hexamethyltriethylenetetramine; tetraethylenepentamine; and pentaethylenehexamine.

14. The composition according to claim 1, wherein the aldehyde is at least one selected from the group consisting of acrolein; senecioaldehyde; glyoxal; malondialdehyde; succinaldehyde; glutaraldehyde; 3-methylglutaraldehyde; 1,6-hexanedial; ethylpentanedial; 1,7-heptanedial; methylhexanedial; 1,8-octanedial; methylheptanedial; dimethylhexanedial; ethylhexanedial; 1,9-nonanedial; 2-methyl-1,8-octanedial; ethylheptanedial; 1,10-decanedial; dimethyloctanedial; ethyloctanedial; dodecanedial; hexadecanedial; 1,2-cyclohexane dicarboaldehyde; 1,3-cyclohexane dicarboaldehyde; 1,4-cyclohexane dicarboaldehyde; 1,2-cyclooctane dicarboaldehyde; 1,3-cyclooctane dicarboaldehyde; 1,4-cyclooctane dicarboaldehyde; and 1,5-cyclooctane dicarboaldehyde.

15. The composition according to claim 1, wherein the polyvalent amine is at least one selected from selected from the group consisting of N,N,N',N'-tetramethyldiaminomethane; ethylenediamine; 1,2-diaminopropane; 1,2-diamino-2-methylpropane; N-methylethylenediamine; N-ethylethylenediamine; N-propylethylenediamine; N-butylethylenediamine; N,N-dimethylethylenediamine; N,N-diethylethylenediamine; N,N-dipropylethylenediamine; N,N-dibutylethylenediamine; N,N'-dimethylethylenediamine; N,N'-diethylethylenediamine; N,N'-dipropylethylenediamine; N,N'-diisopropylethylenediamine; N,N'-di-tert-butylethylenediamine; N,N,N'-trimethylethylenediamine; N,N,N'-triethylethylenediamine; N,N-diethyl-N'-methylethylenediamine; N,N,N',N'-tetramethylethylenediamine; N,N,N',N'-tetraethylethylenediamine; N,N,N',N'-tetraisopropylethylenediamine; N,N,N',N'-tetramethyl-1,2-diaminopropane; 1,3-propanediamine; 2-methyl-1,3-propanediamine; 1,3-diaminobutane; 2,2-dimethyl-1,3-propanediamine; 1,3-diaminopentane; N-methyl-1,3-propanediamine; N-ethyl-1,3-propanediamine; N-propyl-1,3-propanediamine; N-butyl-1,3-propanediamine; N,N-dimethyl-1,3-propanediamine; N,N-diethyl-1,3-propanediamine; N,N-dipropyl-1,3-propanediamine; N,N'-dimethyl-1,3-propanediamine; N,N'-diethyl-1,3-propanediamine; N,N,N'-trimethyl-1,3-propanediamine; N,N,N',N'-tetramethyl-1,3-propanediamine; N,2-dimethyl-1,3-propanediamine; N,N,2,2-tetramethyl-1,3-propanediamine; diethylenetriamine; 2,2'-diamino-N-methyldiethylamine; N,N',N''-trimethyldiethylenetriamine; N,N,N',N'',N''-pentamethyldiethylenetriamine; 3,3'-diaminodipropylamine; N,N-bis[3-(dimethylamino)propyl]amine; triethylenetetramine; 1,1,4,7,10,10-hexamethyltriethylenetetramine; tetraethylenepentamine; and pentaethylenehexamine; and
wherein the aldehyde is at least one selected from the group consisting of acrolein; senecioaldehyde; glyoxal; glutaraldehyde; 3-methylglutaraldehyde; 1,9-nonanedial; and 2-methyl-1,8-octanedial.

* * * * *

UNITED STATES PATENT AND TRADEMARK OFFICE
CERTIFICATE OF CORRECTION

PATENT NO. : 11,434,433 B2
APPLICATION NO. : 16/462065
DATED : September 6, 2022
INVENTOR(S) : M. Shimizu et al.

It is certified that error appears in the above-identified patent and that said Letters Patent is hereby corrected as shown below:

In the Claims

At Column 15, Line 61 (Claim 1, Line 8) please change "hydrogen, atom" to -- hydrogen atom --.
At Column 15, Line 62 (Claim 1, Line 9) please change "carbon;" to -- carbon atoms; --.

Signed and Sealed this
Fourteenth Day of March, 2023

Katherine Kelly Vidal
*Director of the United States Patent and Trademark Office*